(12) United States Patent
Wagner et al.

(10) Patent No.: US 7,468,786 B2
(45) Date of Patent: Dec. 23, 2008

(54) ENGRAVED GEMSTONE VIEWER

(75) Inventors: Randall M. Wagner, Mequon, WI (US); Kurt Schoeckert, Hartford, WI (US)

(73) Assignee: GemEx Systems, Inc., Mequon, WI (US)

( * ) Notice: Subject to any disclaimer, the term of this patent is extended or adjusted under 35 U.S.C. 154(b) by 78 days.

(21) Appl. No.: 11/598,342

(22) Filed: Nov. 13, 2006

(65) Prior Publication Data

US 2007/0109529 A1 May 17, 2007

Related U.S. Application Data

(60) Provisional application No. 60/847,040, filed on Sep. 25, 2006, provisional application No. 60/783,635, filed on Mar. 17, 2006, provisional application No. 60/735,339, filed on Nov. 12, 2005.

(51) Int. Cl.
*G01N 21/47* (2006.01)
*G01N 21/55* (2006.01)
*G01N 21/87* (2006.01)
*G02B 27/02* (2006.01)

(52) U.S. Cl. .................. 356/30; 359/440; 359/801; 359/802; 359/804

(58) Field of Classification Search .................. 356/30, 356/446, 612; 359/798, 801–804, 811, 819, 359/436, 440
See application file for complete search history.

(56) References Cited

U.S. PATENT DOCUMENTS

| | | | |
|---|---|---|---|
| 4,595,095 A * | 6/1986 | Lam .......................... 206/6.1 |
| 5,196,966 A * | 3/1993 | Yamashita .................. 359/896 |
| 6,020,954 A * | 2/2000 | Aggarwal ..................... 356/30 |
| 6,034,826 A * | 3/2000 | Helmecke .................... 359/798 |
| 6,187,213 B1 * | 2/2001 | Smith et al. ................... 216/28 |
| 6,211,484 B1 * | 4/2001 | Kaplan et al. .......... 219/121.68 |
| 6,239,867 B1 * | 5/2001 | Aggarwal ..................... 356/30 |
| 6,684,663 B2 * | 2/2004 | Kaplan et al. .................. 63/32 |
| 6,710,943 B2 * | 3/2004 | Weir .......................... 359/803 |
| 7,010,938 B2 * | 3/2006 | Kaplan et al. .................. 63/32 |
| 7,336,347 B2 * | 2/2008 | Sasian et al. .................. 356/30 |
| 7,372,552 B2 * | 5/2008 | Sasian et al. .................. 356/30 |
| 7,382,445 B2 * | 6/2008 | Sasian et al. .................. 356/30 |

* cited by examiner

*Primary Examiner*—Gregory J Toatley, Jr.
*Assistant Examiner*—Bryan Giglio
(74) *Attorney, Agent, or Firm*—Jeffrey S. Sokol; Cook & Franke S.C.

(57) ABSTRACT

The present invention is an engraved gemstone viewer for viewing a flat, smooth surface of a gemstone that has been micro or nano etched with an inscription such as an identification number. The gemstone is mounted on a piece of jewelry or can remain unmounted when placed inside or otherwise received by the viewer. A source of light directs a light beam toward a magnifying lens coated with a reflection enhancing coating. The lens reflects the light beam along a path incident to the surface of the gemstone containing the inscription. The smooth flat gemstone surface spectrally reflects the light beam along a path back toward the magnifying lens, which produces a viewable light image that reveals the inscription. The inscription is shown as a dark or lightless region of the light image.

17 Claims, 11 Drawing Sheets

ENGRAVED GEMSTONE VIEWER

This application seeks priority on U.S. Provisional Application No. 60/735,339 filed Nov. 12, 2005, U.S. Provisional Application No. 60/783,635 filed Mar. 17, 2006 and U.S. Provisional Application No. 60/847,040 filed Sep. 25, 2006.

BACKGROUND OF THE INVENTION

Identification of polished gemstones and diamonds has been an industry and consumer priority for as long as they have been recognized as unique and valuable. Many gemstones look similar, even upon close examination. Yet, despite their similarity, the value of similar gemstones may vary by a large amount. Historically, diamonds and gemstones of similar size and characteristics have been identified and distinguished apart using a microscope to plot the location and size of imperfections buried in the diamond crystal or gemstone. Unfortunately, these markers are not typically viewable with the naked eye, and in most circumstances it is not practical to have a microscope available to check the markers to properly identify the diamond. Manufacturers, dealers, merchants and consumers have difficulty distinguishing one gemstone from another. As a result, gemstones with significantly different financial value, not to mention emotional value, can be confused. By the time a mistake is noticed, it can be too late to confirm where the mistake took place. As a result, tracking down the gemstones and correcting any mistake can be a difficult or virtually impossible task.

Yet, gemstones are transferred between parties for a variety of reasons. A dealer or retail merchant may transfer a gemstone to another dealer or retailer so that they can show the gemstone to a potential buyer or buyers at different stores or in many different locations. Transfers also occur when a gemstone is mounted in jewelry, and even after a sale when the jewelry is repaired. Consumers are particularly vulnerable because they lack the knowledge and equipment to identify the gems in their jewelry. Still, there is no economical and quick way to identify and confirm that the gemstone being returned from one party is the same as the gemstone given to that party. As a result, companies and people must trust the others that handle their gemstones throughout the distribution, retail and after market channels. This need for trust creates a good deal of anxiety for the person loaning their diamond or gemstone to another. The need for trust leaves the opportunity for one gemstone to be inadvertently mixed up with another, or even to be fraudulently exchanged with another gemstone of lesser value.

Marking diamonds and other gemstones with permanent means has become common practice in the last decade. This includes laser or focused ion beam engraved marks and serial numbers. For example, a common marking method is to micro engrave an inscription on the girdle of the diamond. The girdle is marked to avoid detracting from the natural beauty of the diamond. The girdle is not typically visible after mounting in a piece of jewelry. This engraving is visible with a standard 10× magnification Loupe commonly employed in jewelry stores and diamond traders. While this type of marking is useful during the distribution or retail sale of gemstones, girdle inscription presents a problem with mounted jewelry as the inscription is not typically viewable on the diamond once it has been mounted in jewelry.

A new revolutionary method of marking a polished diamond was recently developed by Norsam Technologies of Portland, Oregon and licensed to the Diamond Trading Company (DTC) formerly known as De Beers. With this method, a microscopic or nano inscription is etched on the table of the diamond via a focused ion beam. The inscription is of such a small size as to be invisible to the naked eye. The inscription is virtually impossible to read even by a skilled jeweler using a common 10× Loupe used by jewelers because the proper viewing angle is difficult to find and the magnification is insufficient. The individual characters (i.e., letters and/or numbers) forming the identification number have a height of about 300 to 500 microns. The inscription is etched to a depth of about 20 to 80 nanometers. The difficulty in viewing the inscription is accentuated by the translucent nature of the diamond and other gemstones, which allows light to pass through both the roughened area formed by the inscription and the surrounding smooth table of the gemstone. The DTC and others have developed viewing systems employing a high 65× magnification camera and an electronic display screen to view the microscopic inscription. Unfortunately, these systems are expensive, cumbersome and complicated to use, which takes away from the value of the inscription because most retail stores and consumers do not have the necessary equipment, and thus cannot see the inscription.

The present invention is intended to solve these and other problems.

BRIEF DESCRIPTION OF THE INVENTION

The present invention pertains to an engraved gemstone viewer for viewing a flat, smooth surface of a gemstone that has been laser etched with an inscription such as an identification number. The gemstone is mounted on a piece of jewelry or can remain unmounted when placed inside or otherwise received by the viewer. A source of light directs a light beam toward a magnifying lens coated with a reflection enhancing coating. The lens reflects the light beam along a path incident to the surface of the gemstone containing the inscription. The smooth flat gemstone surface spectrally reflects the light beam along a path back toward the magnifying lens, which produces a viewable light image that reveals the inscription. The inscription is shown as a darker or significantly light reduced region of the light image.

One advantage of the present gemstone viewer is the clarity of the microscopic inscription revealed by the light image displayed by the viewer. The light image clearly reveals the discrete characters forming the etched identification number on the surface of the gemstone. The viewer uses a simple magnifying lens that magnifies the image without the use of complicated and expensive electronic means, such as cameras and digital processing.

Another advantage of the present gemstone viewer is that the image is viewable by a human eye. The light source is a light emitting diode (LED) that produces a substantially unidirectional light beam. The light source is not a laser that could harm an eye.

A further advantage of the gemstone viewer is that it can take the form of a gift box or display box. The viewer has a compact size and uses of relatively inexpensive components. The viewer is illuminated from the inside by a light source, such as a white LED light. The inside of the viewer is coated with a light absorbing coating such as black paint.

Other aspects and advantages of the invention will become apparent upon making reference to the specification, claims and drawings.

DESCRIPTION OF THE PREFERRED EMBODIMENTS

While this invention is susceptible of embodiment in many different forms, the drawings show and the specification describes in detail several preferred embodiments of the invention. It should be understood that the drawings and specification are to be considered an exemplification of the principles of the invention. They are not intended to limit the broad aspects of the invention to the embodiments illustrated.

Figure 5:
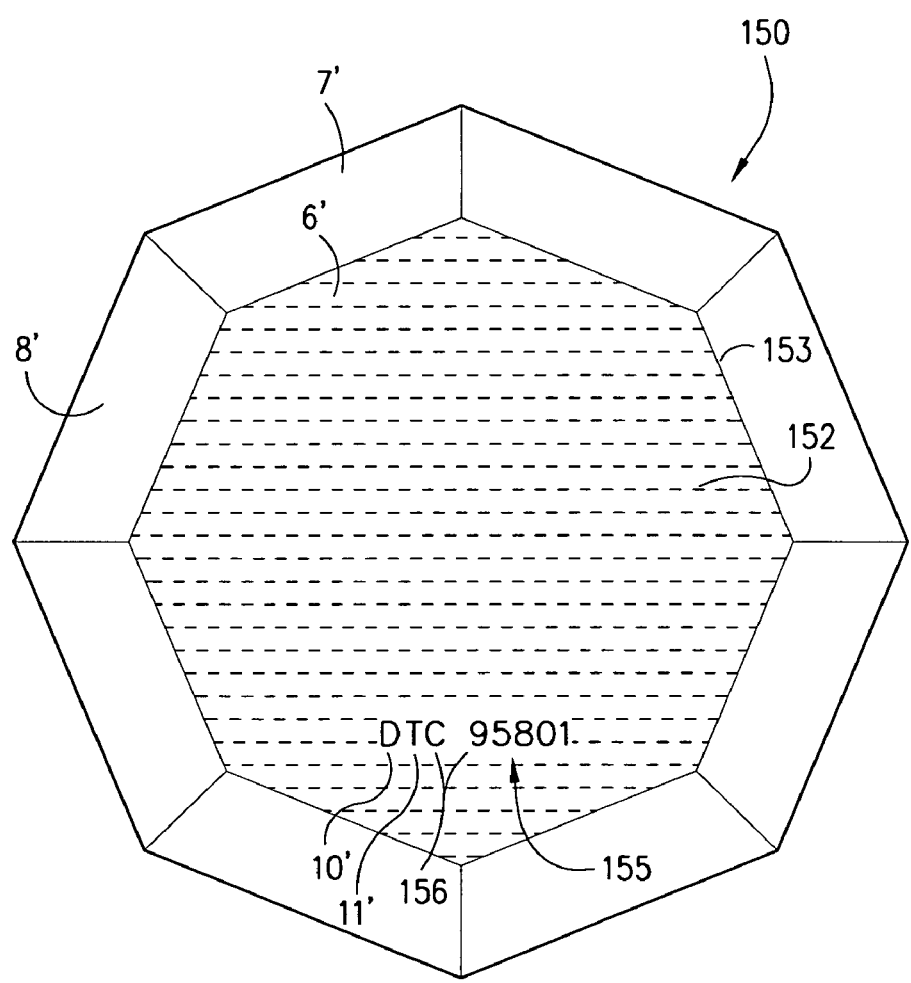
FIG. 5 is an enlarged view of a light image produced by the gemstone viewer where the effective diameter of the unidirectional light beam fills the table of the gemstone held inside the viewer, and where the light image shows the intensity of the light beam in a range of grey to bright white, which is the portion of the light beam that is spectrally reflected by the table of the gemstone, and where the light image reveals distinct characters that form an identification number engraved into the table of the gemstone as dark areas created by an absence of light.

Gemstones 5 such as diamonds have a flat or planar upper surface. This upper surface or table 6 of the gemstone 5 is polished smooth. When the gemstone 5 is viewed from above, the table 6 is centrally located and surrounded by downwardly angled facets 7. The facets 7 slope toward the widest portion or girdle 8 of the gemstone 5. The shape of the gemstone 5 defines its center 9 when viewed from above as in FIG. 5. The center 9 of the gemstone 5 is generally the center of its table 6. Typical gemstones 5 have a table 6 with a diameter in the range of about 2 mm to 12 mm (millimeters). To avoid confusion, the smooth surface of the table 6 is micro or nano etched to form an engraving or inscription 10 such as an identification number 11 into the table 6. Jewelry pieces 15 such as rings, necklaces and pendants typically engage the girdle 8 to secure the gemstone 5. The table 6 is left unobstructed and readily viewable. A name, logo, slogan, or trademark of the manufacture of the gemstone 5 or jewelry piece 15, or a personalized message or picture of a consumer, can also be etched into the table 6 for identification and marketing purposes. Although the etching process and inscription 10 disrupt the otherwise smooth surface of the table 6, the size, nature and depth of the micro or nano etching renders the inscription 10, identification number 11, mark or logo virtually invisible to the naked or unaided human eye, and does not inhibit the overall beauty, sparkle or scintillation of the gemstone 5 when viewed through its table 6.

The present invention generally relates to an engraved gemstone viewer that is generally shown as reference number 20 in FIGS. 1-4. The gemstone viewer 20 has an outer shell 21 in the shape of a globe. The shell 21 has outer and inner surfaces 22 and 23. The outer surface 22 is generally smooth, and intended to be held and gripped by a person. The inner surface 23 is coated with a light absorbing coating 24, such as black paint. The shell 21 is hollow and defines an interior space 25 for receiving, holding and enclosing the gemstone 5 or jewelry piece 15. The shell or globe 21 has a central axis 27, and is generally formed by two half shells 31 and 41. Each half shell 31 or 41 is preferably an integrally molded piece of plastic having the shape of a hemisphere. Each shell has a wall thickness of about 1/16. The diameter of the globe 21 is preferably about 4½ inches to accommodate a wide variety of jewelry pieces 15.

The lower shell 31 is structured to receive and hold the stone 5 or jewelry piece 15. The shell 31 has a central, circular opening 32 and a planar outer rim 33. The opening 32 receives a focusing assembly, as discussed below. The inside surface 23 of the lower shell 31 has an inwardly projecting annular flange 34. This annular flange 34 is positioned around the central opening 32. A pair of opposed alignment legs 35 extend from the annular flange 34 and further into the interior 25 of the lower shell 31. At least one of the alignment legs 35 has a linear channel or slot 36 formed into its inwardly facing surface. The central opening 32, annular flange 34 and alignment legs 35 combine to form an alignment slot 38 for receiving and holding the focusing assembly. The bottom of the lower shell 31 is shaped to form a planar flange 39. This planar flange 39 has a flat bottom or outer surface.

The upper shell or dome 41 is structured to receive and enclose the gemstone 5 or jewelry piece 15, and is removably secured to the lower shell 31. Similar to the lower shell 31, the upper shell 41 has a central, circular opening 42 and a planar outer rim 43. The central opening or viewing portal 42 is diametrically opposed to and in axial alignment with the central opening 32 of the lower shell 31. The centers of both openings 32 and 42 are located on and define the central axis 27 of the viewer 20. The rim of each half shell 31 and 41 is shaped to matingly receive the rim of the other half shell to form the full globe 21. The upper shell 41 is designed to snap fit to the lower shell 31, and to allow it to rotate about the lower shell when so secured. The upper shell 41 includes four inwardly extending, equal length, mounting arms 45. Both shells are made of a hard plastic material to retain their shape, and are opaque to block ambient outside light from entering the globe 21 during use.

A magnifying glass or lens 50 is received by the central opening 42 of the upper shell 41. This lens 50 has upper and lower convex surfaces 52 and 53. The magnifying glass 50 is a conventional convex lens made of glass or plastic. The lens 50 has a diameter of about 20 mm, and an optical magnification in the range of 14× to 20×. When the magnification is 18×, the focal length to read the inscription 10 on the gemstone 5 is about 0.6 inches. The center of the lens 50 is located on the axis 27 of the viewer 20. The outer perimeter of the lens 50 fills the central opening 42 and is flushly and matingly received by the edges of the shell 41 forming the central opening. When the shell halves 31 and 41 are joined together, the viewer 20 is generally designed to prevent ambient light from entering its interior 25. Although some ambient light can enter through the viewing lens or eyepiece 50, this light is relatively small and has a negligible effect given the internal light absorbing coating 24 and the much larger amount of light emitted from the internal light source 60 of the viewer 20. A reflective enhancing coating 55 is applied to the entire underside 53 of lens 50. This coating 55 is a conventional metallic reflective coating applied to the lens by vacuum deposition. The coating 55 reflects some light and allows some light to pass through the coating and lens 50. The reflective coating 55 has about a 50/50 beam split, or is about 50 percent reflective and 50 percent transmissive. The lens 50 is not covered with the light absorbing coating 24.

Figure 1:
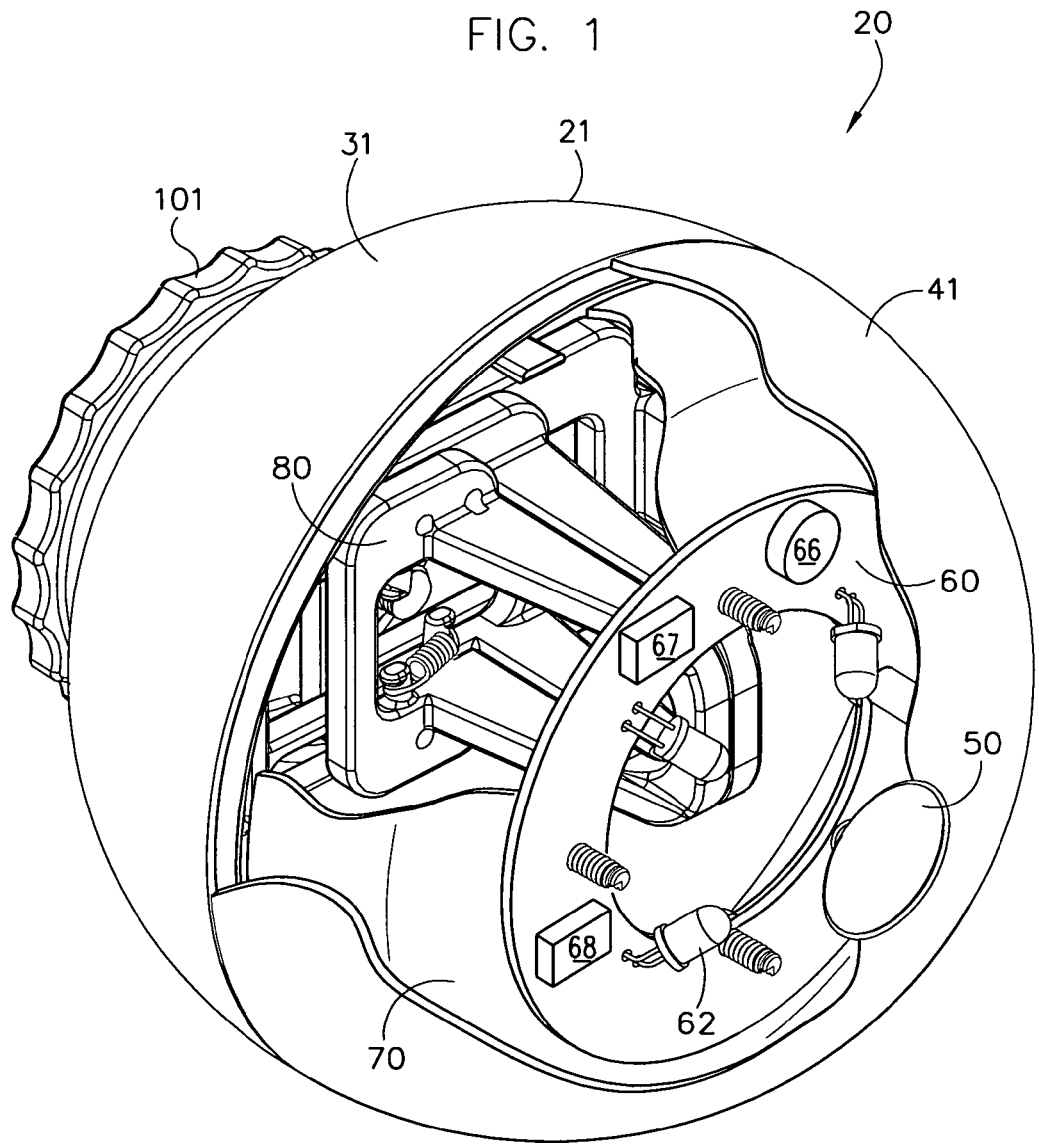
FIG. 1 is a perspective view showing an embodiment of the engraved gemstone viewer with a portion of the upper shell cut away to show the gemstone gripping assembly and light source.
Figure 2:
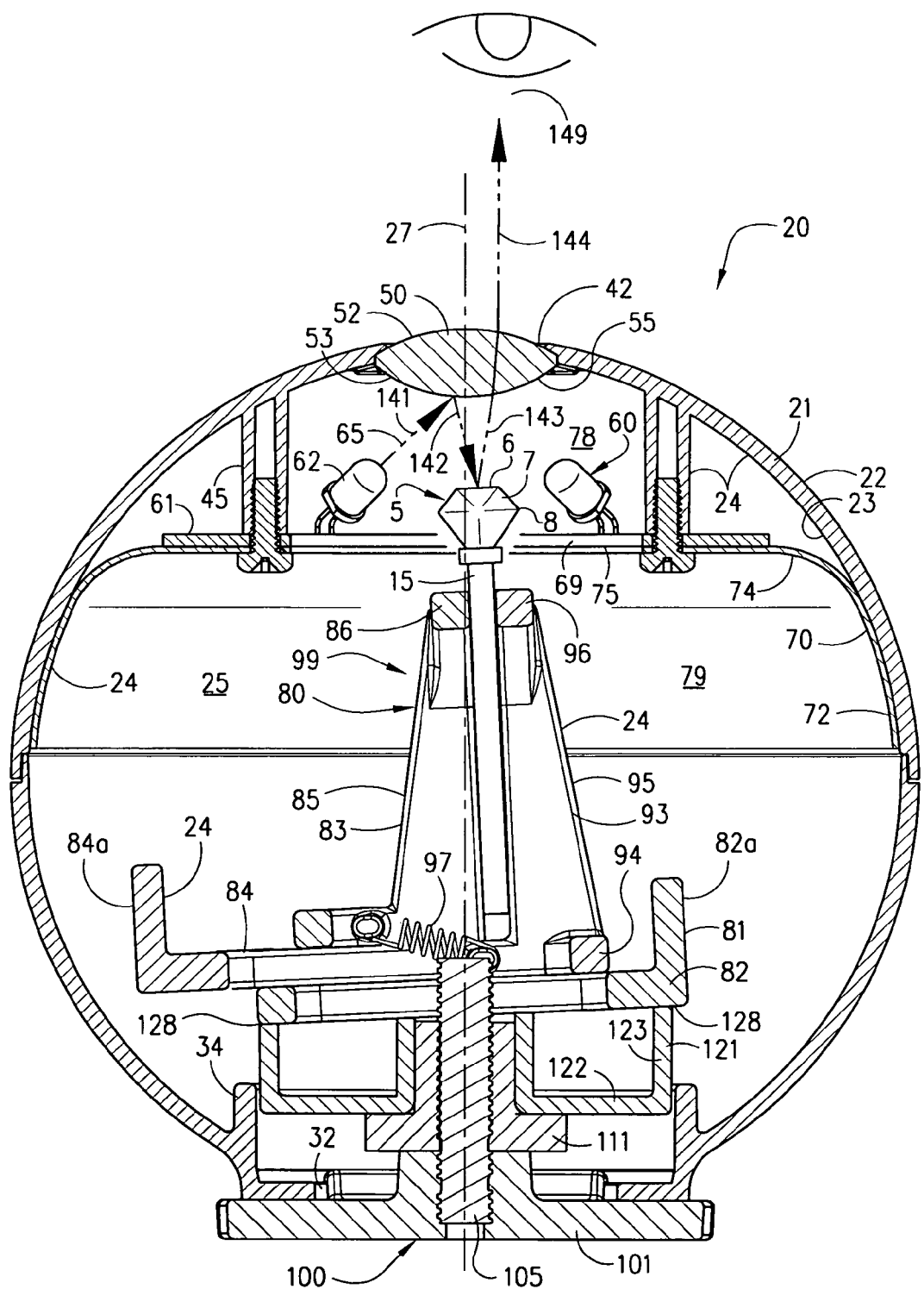
FIG. 2 is a side sectional view of the viewer showing the gemstone gripping assembly holding a diamond ring positioned by the focusing assembly so that each of the unidirectional LED lights emit a beam of light that travel along a path from the LED light up to the lens, reflect off the lens and down onto the table of the diamond, and then reflect off the diamond and up through the lens to the eye of a person.
Figure 3:
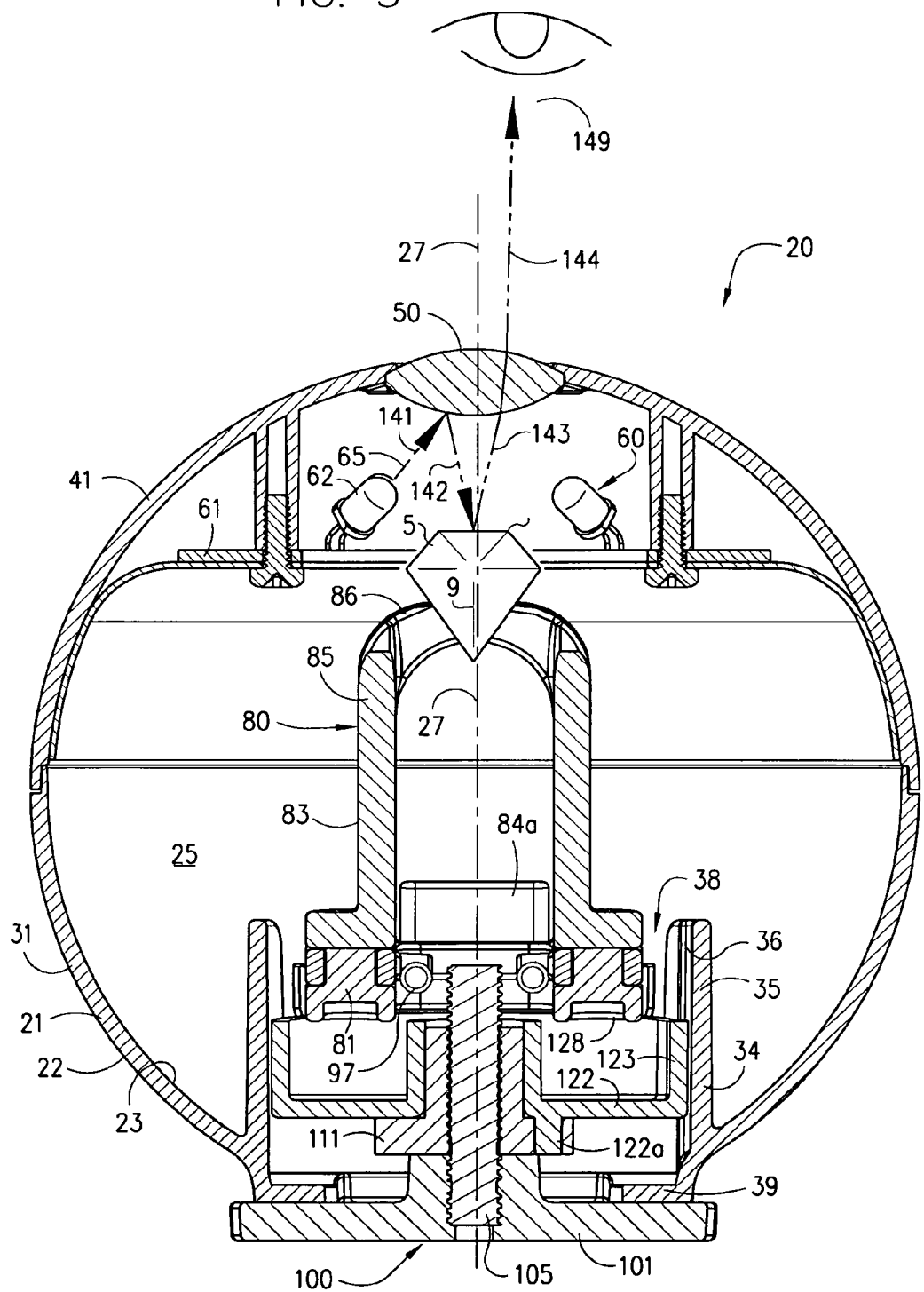
FIG. 3 is a second side sectional view of the viewer holding an unmounted diamond and showing the light path.

The upper shell or dome 41 carries the internal light source 60 of the viewer 20. The light source 60 is formed by a circuit board 61 with four light emitting diode (LED) lights 62. Each LED light 62 emits white light from its tip as a generally unidirectional beam of light 65 as shown in FIGS. 2 and 3, similar to a flashlight where the majority of the light or photons remain substantially parallel to the path of the beam over a useful distance. Each LED light 62 has a tip diameter of about 5 mm, and emits a light beam 65 of about that diameter with the beam diameter spreading a bit as it travels away from its source 62. Each substantially unidirectional light 62 operates at about 3.7 volts, has a maximum luminous intensity of about 4,400 millicandela, and produces a light beam 65 having a cone of divergence of about 10 degrees. The lights 62 are preferably conventional LED lights of the type manufactured by Lite-On, Inc., of Milpitas, California, and sold as Model No. LTL33BCWK5AT. The cone of divergence of the light beam 65 increases to greater than 10 degrees after the beam reflects off the convex surface 53 of the lens 50, as discussed below. Although the light 62 is described as being a white light, it should be understood that the light could be a specific color or filtered in some manner without departing from the broad aspect of the invention.

The LED lights 62 are in electrical communication with a battery 66 via the circuit board 61. The circuit board 61 includes a motion or G-force switch 67 and a timing circuit 68. The motion switch 67 activates the light source 60 when it senses the physical movement of the upper shell 41. The timing circuit 68 turns off the light source 60 after a desired period of time. The conventional LED lights 62, battery 66, switch 67 and timer 68 are electrically and cooperatively connected via the circuit board 61. The generally planar circuit board 61 is mounted generally normal to the axis 27 of the shell 41 via positioning post 45 and fasteners such as screws. The circuit board 61 has a circular, central opening 69 with a diameter of about 1¾ inches. The center of the opening 65 is located on the central axis 27 of the viewer 20, so that the opening 69 is generally parallel to and in aligned registry with the magnifying lens 50. The LED lights 62 are spaced equidistantly apart around the central opening 69. Each light 62 is aimed with its tip facing toward the lens 50 so that its emitted light beam is directed at the lens as in FIGS. 2 and 3.

In the globe viewer embodiment shown in FIGS. 1-4, the tip of each light 62 is located about ¾ inches from the central axis 27 of the viewer 20, and the center line of the light beam 65 is about ½ inch from the point that center line strikes the surface of the lens 53. However, it should be understood that these dimensions can change without departing from the broad aspects of the invention. In addition, although the viewer 20 is shown with four LED lights 62, it should be understood that the viewer can have a single light. While the use of a viewer with multiple lights 62 helps the operator find and position one light beam 65 on the gemstone table 6 so that a mirrored image is viewable at a focal point along the central axis 27 of the viewer 20 as discussed below, it should be understood that only a single light 62 is needed to produce the mirrored image seen by the operator as in FIG. 5. A drawback of a multi-light 62 viewer 20 is that it tends to decrease the clarity of the etching 10 or identification number 11 revealed by the mirrored image.

The upper shell 41 includes a circuit board cover 70. This cover 70 has a curved outer portion 72 shaped so that its outer surface flushly engages and presses against the inner surface 23 of the upper shell 41. The cover 70 also forms a generally linear wall 74 located directly below and pressing against the lower surface of the circuit board 61. The cover 70 has a circular, central opening 75 that has the same diameter as, and is in axial alignment and registry with, the opening 69 of the circuit board 61. Light emitted from the LED lights 62 reflects off the magnifying lens 50 to pass through openings 69 and 75. The circuit board 61 and its cover 70 divide the interior 25 formed by the upper shell 41 into an upper, light emitting chamber 78 and a lower, diamond chamber 79. In this embodiment, the LED lights 62 are aimed so that their light beams 65 do not pass directly through central openings 69 and 75 and into the diamond chamber 79 until the light beam 65 reflects off the magnifying lens 50. Similar to the inside surface 23 of the shells 31 and 41, and the other internal components of the globe 20, the circuit board 61 and its cover 70 are preferably coated with a light absorbing material 24 such as black paint.

Figure 4:
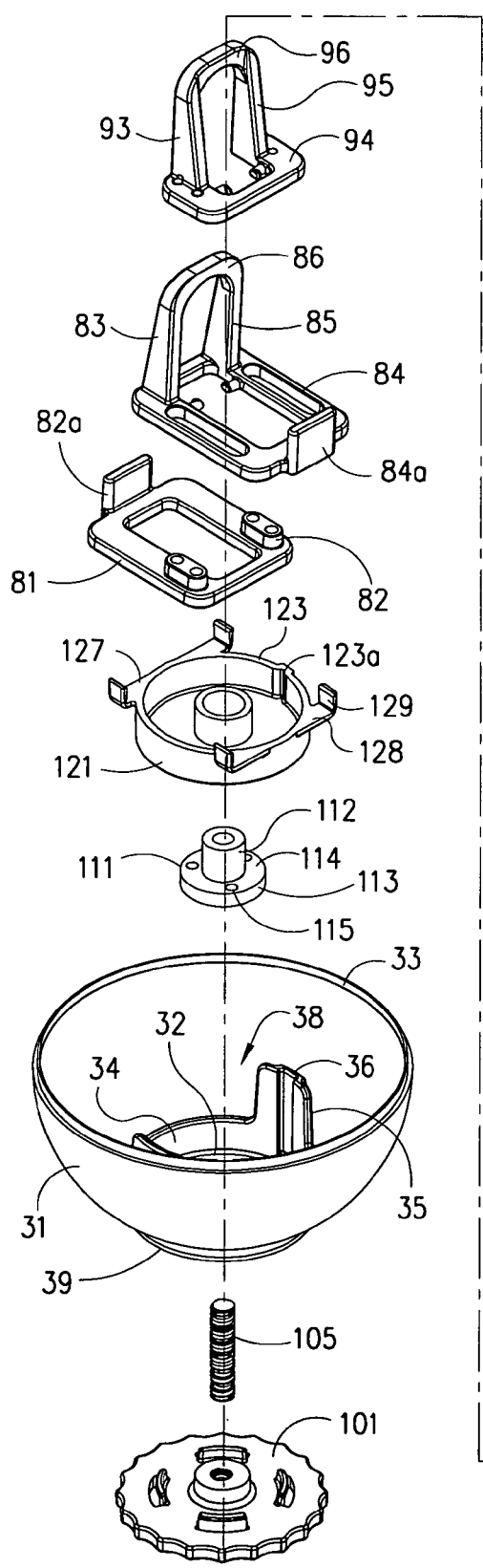
FIG. 4 is an exploded view of the engraved gemstone viewer.
Figure 4:
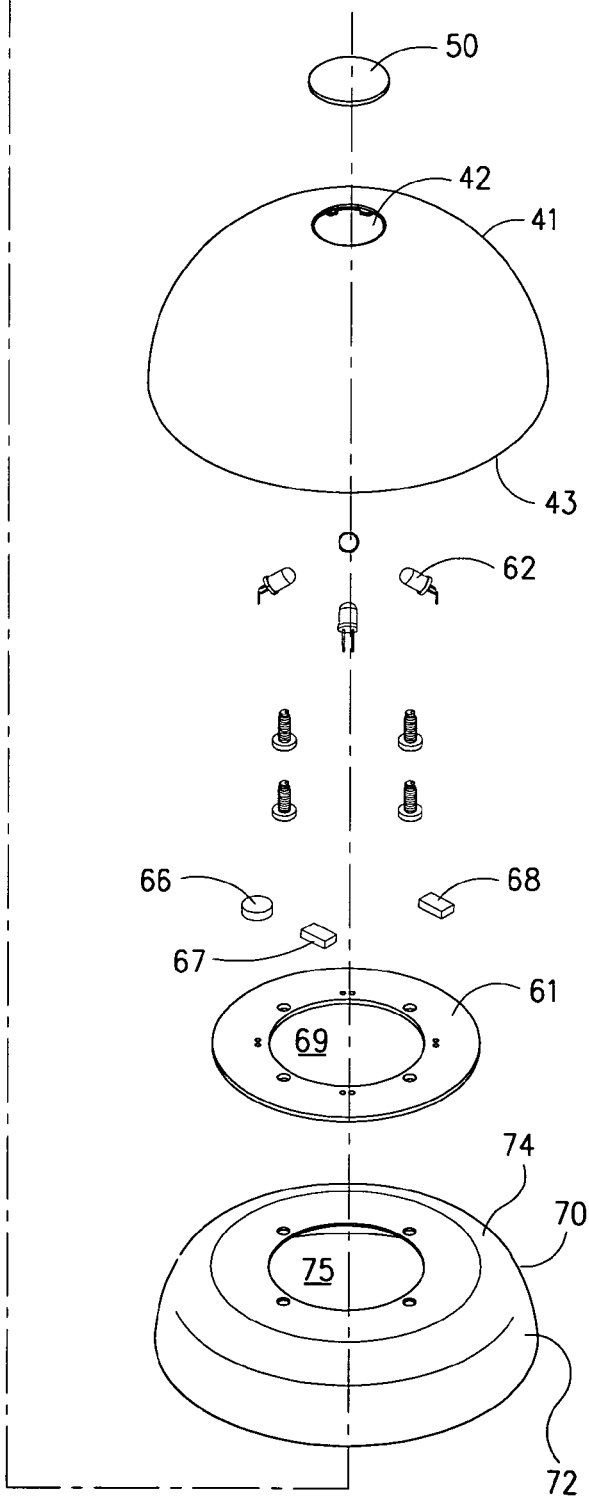
Figure 6:
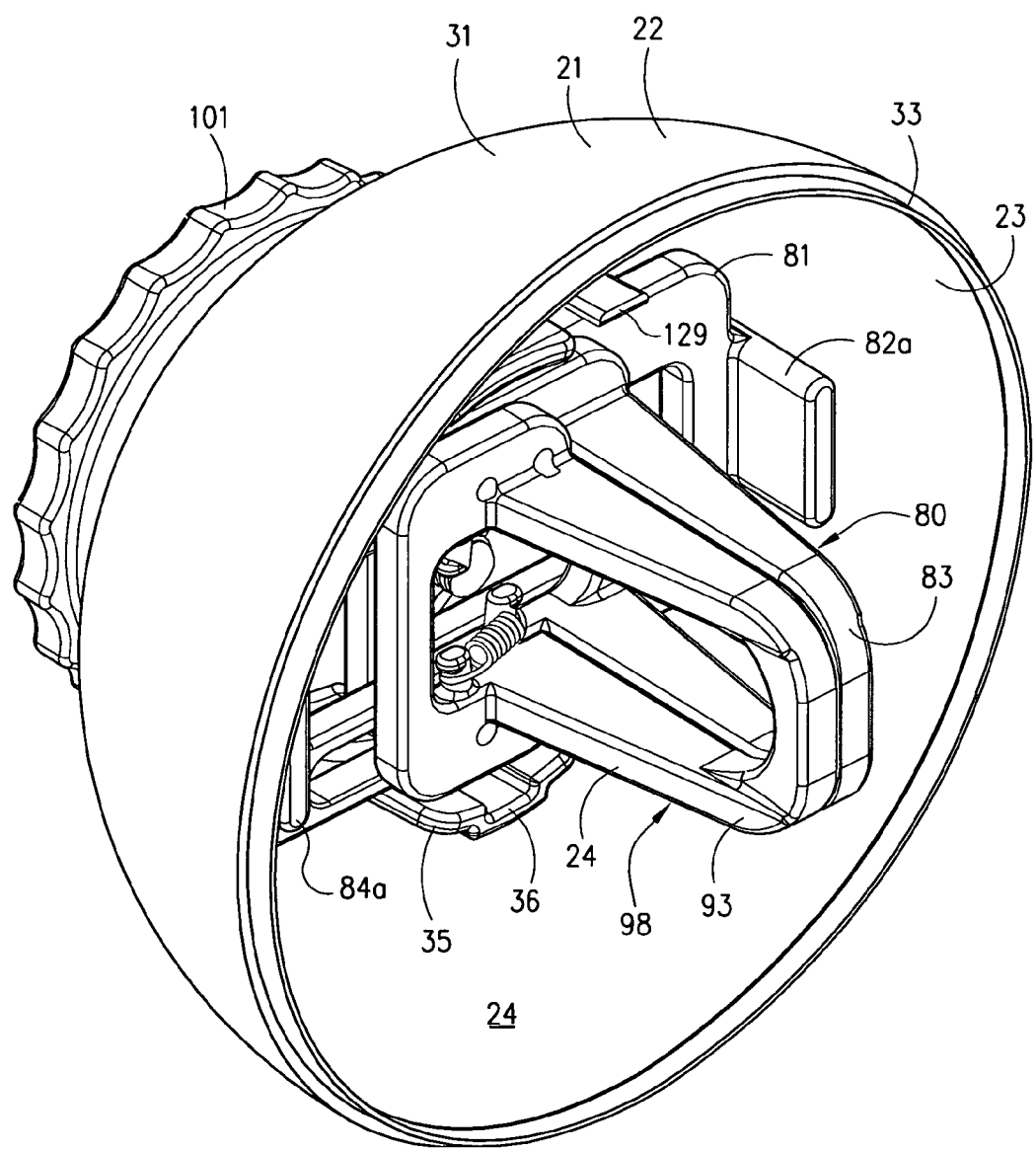
FIG. 6 is a perspective view of the gemstone viewer with the upper shell removed to gain access to the inside of the viewer and the diamond gripping assembly.
Figure 7:
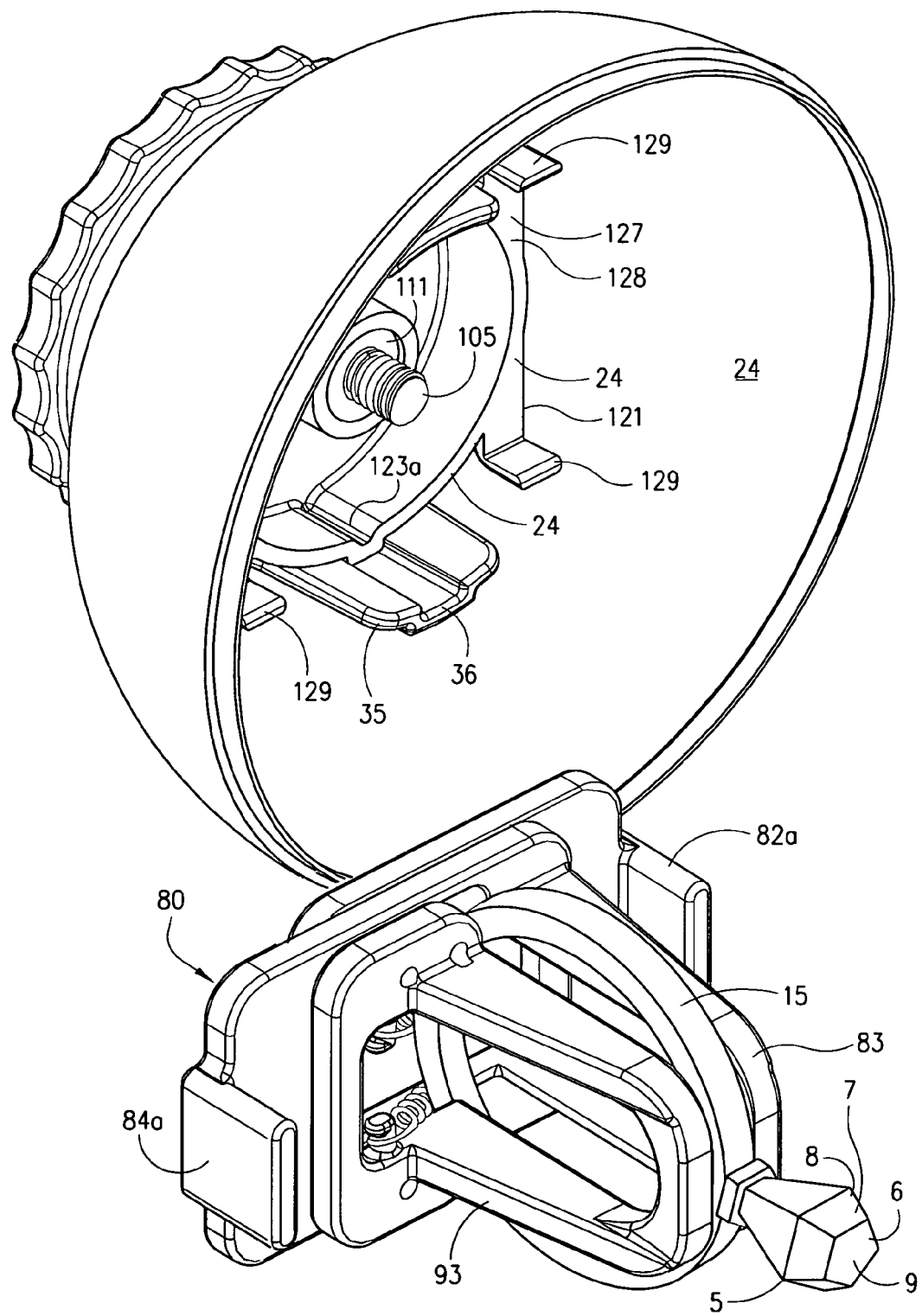
FIG. 7 is a perspective view of the gemstone viewer with the upper shell removed and with the gripping assembly taken out from the lower shell to affix a diamond ring held by the gripping assembly.

The engraved gemstone viewer 20 is adapted and configured to receive a gemstone mounting gripping assembly 80 best shown in FIGS. 4, 6 and 7. The gripping assembly 80 includes a lower mounting bracket or plate 81 with an open center. This bracket 81 has a generally flat upper surface with two upwardly projecting posts 82 located proximal one end. The other end of the bracket 81 has a push plate 82a. The bracket 81 holds a pair of clamps 83 and 93. The lower clamp 83 is slidingly mounted to the upper surface of the bracket 81. The clamp 83 has a pair of horizontal slide bars 84 with an open center. Each slide bar 84 has an elongated slot. One end of the slide 84 has a push plate 84a. The other end of the slide 84 has an upwardly extending U-shaped gripping arm 85 with an upper gripping portion 86. The upper clamp 93 has a lower plate 94 with slots adapted to lockingly receive posts 82. The clamp 93 includes an upwardly extending U-shaped gripping arm 95 with an upper gripping portion 86. The upper gripping portions 86 and 96 of the arm 85 and 95 are structured to grip a single, unmounted gemstone 5 as shown in FIG. 3, or a jewelry piece 15 such as in a ring as in FIG. 2. A set of two springs 97 bias the gripping assembly 80 into a closed position 98 as in FIG. 6. One end of each spring 97 is secured to the lower clamp 83 and one end of each spring is secured to the upper clamp 93. By squeezing push plates 82a and 84a together, the gripping assembly 80 moves to its open position 99 as in FIGS. 2, 3 and 7.

The gemstone viewer 20 includes a focusing assembly 100 best shown in FIGS. 2-4. The focusing assembly 100 is received by the central opening 32 and alignment slot 38 of the lower shell 31. The assembly 100 includes a focusing wheel 101 that is generally flat with a central hub and outer ribbed rim that extends away from the globe 21 for easily gripping. The hub has a flat centrally upper surface in flush, rotatable engagement with the flat lower surface of the planar flange 39 of shell 31. The wheel 101 is threadably and rigidly secured to a focusing screw or rod 105. The rod 105 is in coaxial alignment with the central axis 27 of the viewer 20. The rod 105 threadably and rotatably receives an adjustable focusing nut 111. The nut 111 has a thinner upper portion 112 and a thicker lower portion 113 to define a horizontal ledge 114 with a number of recesses 115.

The adjustable focusing assembly 100 includes a platform or carriage 121. This carriage 121 includes a lower web 122 with downwardly projecting locking studs 122a that are matingly received into the recesses 115 in the nut 111 to fix the nut to the carriage. The platform 121 includes an outer annular flange 123 having a diameter sufficient so that it engages the alignment legs 35 of the lower shell 31. The outer flange 123 includes an anti-rotation key 123a that is slidably received in the linear channel 36 of one alignment leg 35. The keyed engagement of key 123a into slot 36 prevents the rotation of both the platform 121 and nut 111, so that rotation of the adjustment wheel 101 and rod 105 do not rotate the nut 111 or carriage 121. Instead, the focusing nut 111 and carriage 121 move linearly upwardly or downwardly along the adjustment rod 105, or in other words along a linear path of travel coaixial to the central axis 27 of the viewer 20. The carriage 121 includes an inner flange 124 that defines a central opening for snugly receiving the upper portion 112 of nut 111. The platform 121 also includes an outer frame 127 with a flat upper surface or platform 128 for flushly receiving and supporting the lower surface of the mounting plate 181 of the gemstone mounting assembly 80. The outer frame 127 includes four corner posts 129 spaced to snugly receive the sides of the mounting plate 81 to hold the gripping assembly 80 in place when secured to the focusing assembly 100. As indicated above, the gripping assembly 80 and focusing assembly 100 are preferably coated with a light absorbing material 24 such as black paint.

The platform 128 is sloped or angled about five degrees (5°) out of normal to the central axis 27 as in FIG. 3. When resting on the platform 128, the gripping assembly 80 is also tilted this same angle, so that the table 6 of the gemstone 5 is also tilted this same angle so as to be angled toward the direction of a selected incoming light beam 65. The gripping assembly 80 is positioned on the platform 128 so that the table 6 of the gemstone 5 remains aligned with the central axis 27 of the viewer 20. Although the platform 128 and gemstone table 6 are shown tilted to help produce a mirrored image 150 at a focal point 149 along the central axis 27 of the viewer 20, it should be understood that the broad aspect of the invention also applies to viewers that position the gemstone table 6 normal to the central axis of the viewer.

Light is emitted from the LED light or lights 62 such that each light beam 65 travels along a path 141 towards the magnifying lens 50 as shown in FIGS. 2 and 3. Each light beam 65 strikes a portion of the lower convex surface 53 of the lens 50, and is reflected to travel down along a path 142 toward or incident to the table 6 of the gemstone 5 held by the gripping assembly 80. Given the lens surface 53 is highly polished and smooth and has a reflection enhancing coating 55, the light beam 65 reflects off the lens surface 53 in a manner resembling specular reflection, although the slight curvature of the convex surface 53 causes some additional spreading of the light beam 65 or its cone of divergence. Still, much of the reflected light traveling along incident path 142 maintains a substantially defined beam shape containing substantially unidirectional light. Given the table 6 of the gemstone 5 is very flat, and highly polished and smooth, the light beam 65 strikes the table 6 from above in a specularly reflective manner so that the integrity of the reflected unidirectional light beam 65 is maintained when traveling along specularly reflected path 143.

The etched region or inscription 10 of the table 6 reflects the light beam 65 in a diffuse reflection manner. The portion of the light beam 65 traveling along incident path 142 that strikes the inscription 10 on the gemstone 5 is reflected in a diffuse or scattered manner away from path 143. This diffusely reflected portion of the light beam 65 does not travel along the same path 143 as the specularly reflected portion of the light beam 65. Thus, the diffusely reflected portion of the light beam 65 is not directed at the lens 50, and is absorbed by the light absorbing coating 24 covering the surfaces inside the globe 21. The specularly reflected portion of the light beam 65 is reflected to travel up along path 143 back towards lens 50. While the total diameter of the light beam 65 is larger than 5 mm when it strikes and reflects off the gemstone table 6, the effective or useful diameter of the light beam for producing a spectrally reflected light image 150 via specular reflection is believed to be about 5 to 6 mm.

The reflected light beam 65 traveling along specularly reflected path 143 is gathered by the lens 50 and directed along a focused path of travel 144 towards a focal point 149 for viewing. The focal point 149 is located in axial alignment with and a distance of about two to three inches above lens 50. When viewing the gemstone 5 through the viewer 20 at its focal point 149, the viewer displays a light image 150 containing white light region 152 as in FIG. 5. When the unidirectional light beam 65 striking the table 6 of the gemstone 5 is large enough to cover the entire surface of the table, the light image 150 shows the lighted region 152 in a distinct pattern having an angled perimeter 153 depicting the angled perimeter of the gemstone table 6 being viewed. The lighted region 152 is formed by the spectrally reflected light of the light source 60. The lighted region 152 includes a dark region 155 containing the individual characters or discrete component areas 156 representing the inscription 10 or identification number 11 engraved into the table 6 of the gemstone 5. The disruption of the otherwise flat, smooth surface of the table 6 caused by the inscription 10, disrupts the light reflected by the inscription so that portion of the light does not travel along paths 143 or 144 to the focal point 149. Thus, the inscription portion 10 of the light image 150 viewed at the focal point 149 is shown as dark characters 156 formed by an absence of light in the lighted region 152.

The table 6 of the gemstone 5 is positioned at the internal focal point 148 so that the light image 150 at external focal point 149 produces discrete representations of the characters 154 forming the inscription 10 of identification number 11. The geometric configuration and orientation of the lens 50 and lights 62, as well as the size of the characters 154 forming the inscription 10 or identification number 11 dictate the position of the internal focal location 148 In this embodiment, the focal location 148 is about ½ to ¾ inches from the lens, but can differ in other embodiments without departing from the broad aspects of the invention. By turning the focusing wheel 101, the focusing nut 111 and carriage 121 move the gripping assembly 80 and gemstone 5 along a linear path of travel coaixial to the central axis 27 of the viewer 20, so that the gemstone moves closer to or further away from the lens 50 and into the desired focal location 148.

Figure 8A:
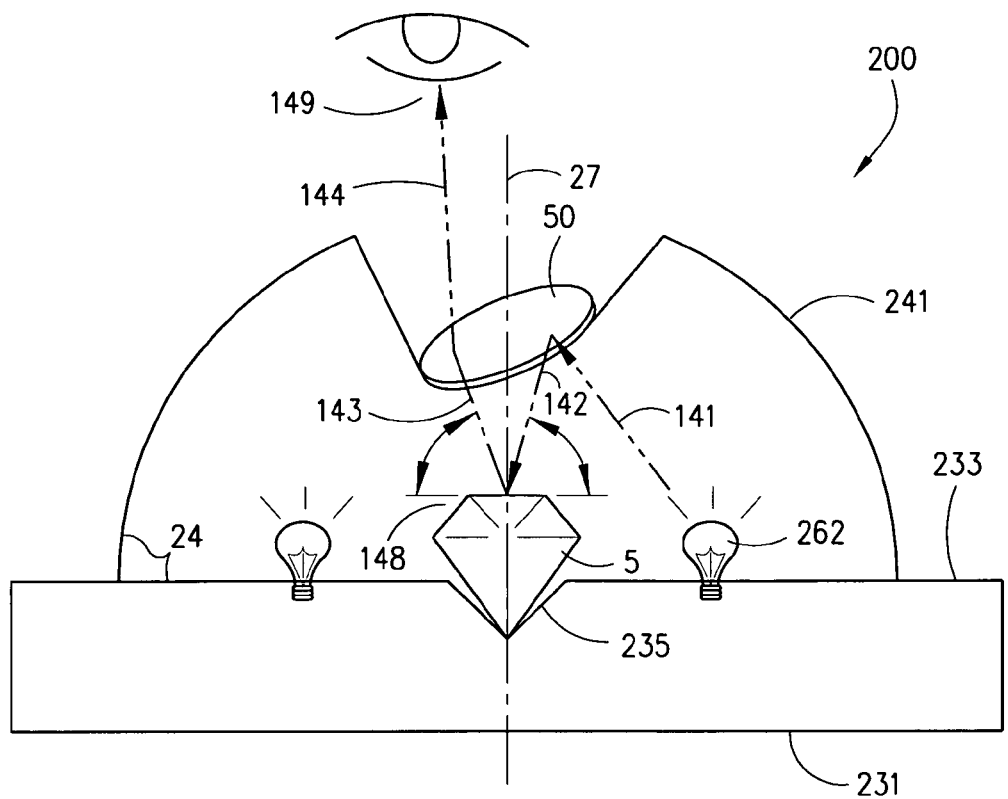
FIG. 8A is a side plan view of a second embodiment of the engraved gemstone viewer with a half sphere configuration and a single magnifying lens.

A second embodiment of the engraved gemstone viewer 200 is shown in FIG. 8A. The viewer 200 has a single half shell construction that incorporates a flat base 231 and an upper shell or dome 241. The base 231 has a flat, horizontal, upper surface 233 to receive and fixedly mount the gemstone 5. The base 231 also holds the light source 60. The viewer 200 is designed to rest on a flat supporting surface for stability during use. The bottom of the base 231 is flat for that purpose. The gemstone 5 is placed in a central notch 235 located along the central axis 27 of the viewer 200. The notch 235 is shaped to position the gemstone 5 with its table 6 substantially planar to the surface 223 of the base 231. The center portion of the upper shell 241 is recessed to bring the lens 50 closer to the gemstone 5 for focused viewing. The light source 60 is similar to that of viewer 20, and includes a circuit board, battery, motion switch and central opening.

Figure 8B:
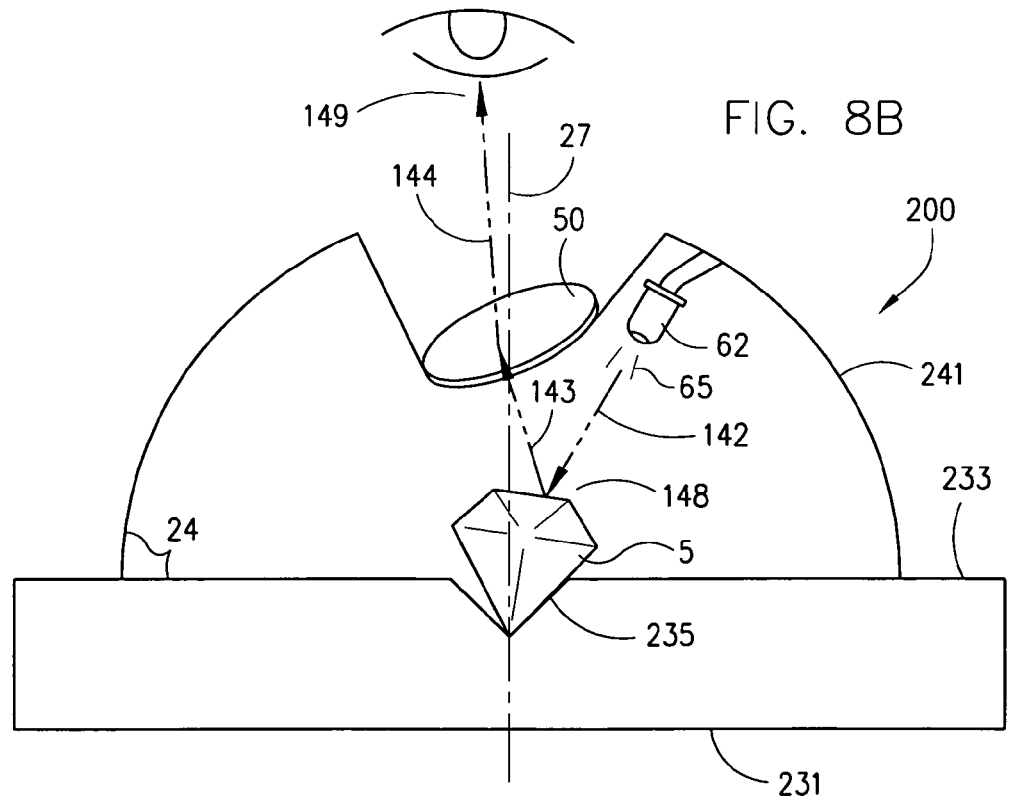
FIG. 8B is a side plan view of a modified version of the second embodiment with an LED light positioned above the gemstone table and aimed to direct its light beam directly onto the gemstone table.

The lights 262 are conventional multidirectional incandescent bulbs, but could also be unidirectional lights 62. The lights 262 are evenly spaced around the gemstone 5, and are located below its table 6 so that light they emit does not directly strike the table. The inside of the viewer 200 includes the light absorbing coating 24. The lens 50 is of the same general type as in the globe shaped viewer 20, and includes the refection enhancing coating 55. A modified version of this embodiment is shown in FIG. 8B. In this version, the gemstone 5 is tilted or angled out of alignment with the central axis 27 of the viewer 200 so that its table 6 faces toward an LED light 62 secured to the upper portion of the upper shell 241. The light 62 is located above the table 6 of the gemstone 5, and its unidirectional light beam 65 is aimed directly at the gemstone table 6.

The light paths 141-144 are basically the same as above, and spectrally reflected light image 150 of the light source 60 to reveal the inscription 10 on the table 6 of the gemstone 5 is produced in basically the same manner. The lens 50 is fixed to the upper shell 241 with center of the lens 50 on the central axis 27 of the viewer 200. However, the lens 50 is mounted in an angled position so that its optical axis is angled from the central axis 27. The upper shell or dome 241 is rotated about the base 231 to help bring the table 6 of the gemstone 5 to the focal location 148 and the light image 150 and characters of the inscription 10 into focus.

Figure 9:
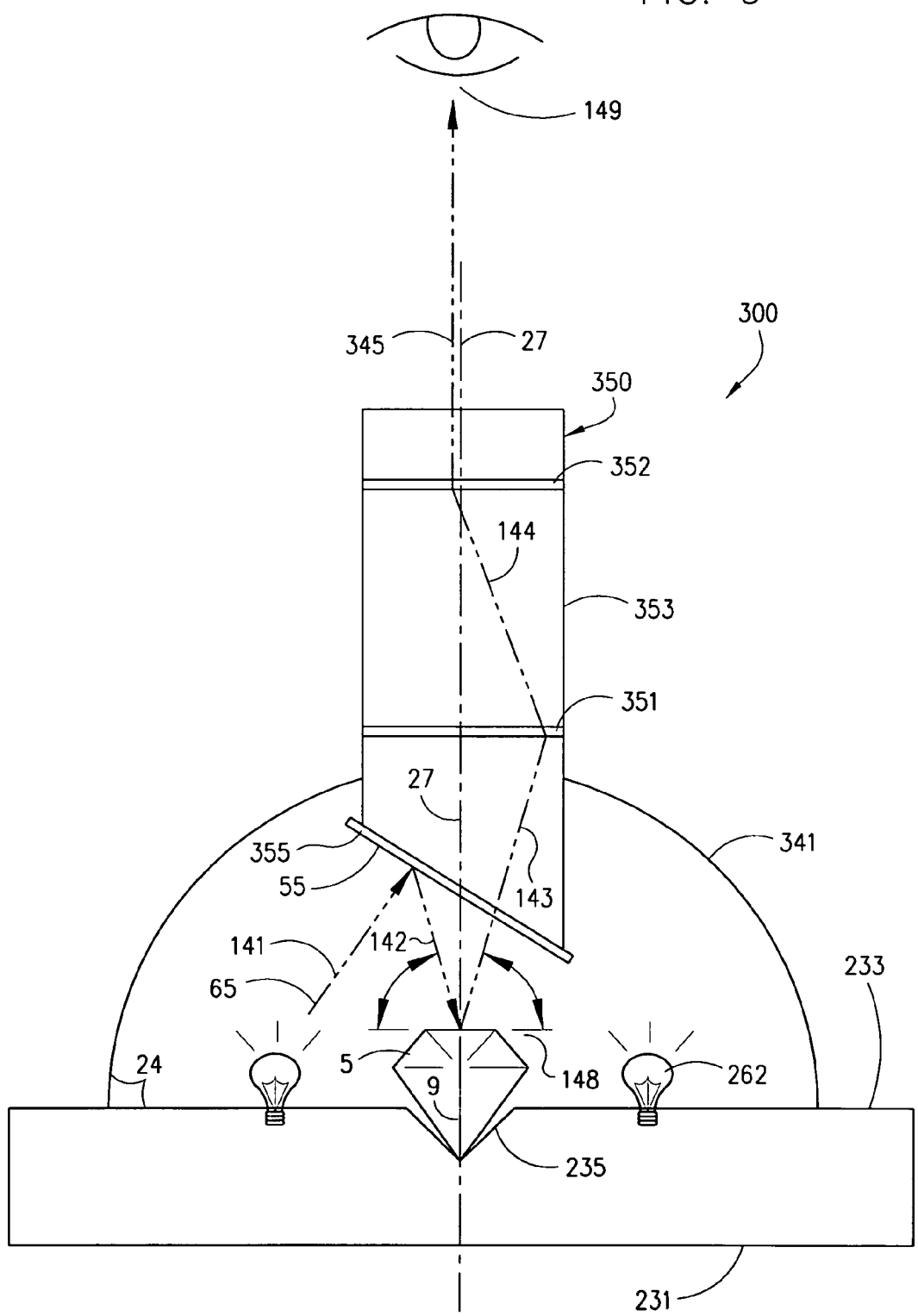
FIG. 9 is a side plan view of a third embodiment of the engraved gemstone viewer with a half moon configuration and a scope having two magnifying lenses and a glass plate at the end of the scope.

A third embodiment of the engraved gemstone viewer 300 is shown in FIG. 9. This viewer 300 incorporates a microscope device 350. The viewer 300 has single half shell construction that incorporates a flat base 231 similar to that of viewer 200, and a modified upper shell or dome 341 that holds a microscope device 350. The base 231 has an upper surface 223 for fixedly mounting the gemstone 5 and securing a light source 60. The inside of the viewer 200 includes the light absorbing coating 24.

Similar to viewer 200, the gemstone 5 is placed in a central notch 235 located along the central axis 27 of the viewer 300. The notch 235 is shaped to position the gemstone 5 with its table 6 substantially planar to the surface 223 of the base 231. The light source 60 is similar to that of viewer 20, and includes a circuit board, battery and central opening. The lights 262 are conventional multidirectional incandescent bulbs, and not unidirectional. The lights 262 are evenly spaced around the gemstone 5, and are located below its table 6 so that the light they emit does not directly strike the table. Light paths 141-144 are similar to viewers 20 and 200, but include an additional path 345 given the two lenses 351 and 352. The spectrally reflected image 150 of the light source 60 revealing the inscription 10 on the table 6 of the gemstone 5 is basically the same.

The microscope device 350 has two spaced apart lenses 351 and 352 held by a tube 353. The lenses 351 and 352 are of the same general type as the lens 50 in the globe shaped viewer 20. The distance between the lenses 351 and 352 is adjustable to bring the inscription 10 on the gemstone into focus. A glass plate 355 with the reflection enhancing coating 55 on its lower surface is secured to the lower end of the device 350. This end of the microscope 350 passes through the portal 42 of the viewer 300 so that the glass plate 355 is located inside 25 the viewer. The centerline of the microscope device 350 is located along the central axis 27 of the viewer 300 with its optical axis coaxially aligned with the central axis 27 of the viewer. The microscope device 350 is rotatable relative to the gemstone 5. The microscope device 350 is rigidly secured to the upper shell 341. The shell 241 and microscope device 350 are rotatable relative to the base 231. This helps bring the table 6 of the gemstone 5 to the focal location 148, and the image 150 and inscription 152 into focus.

Figure 10:
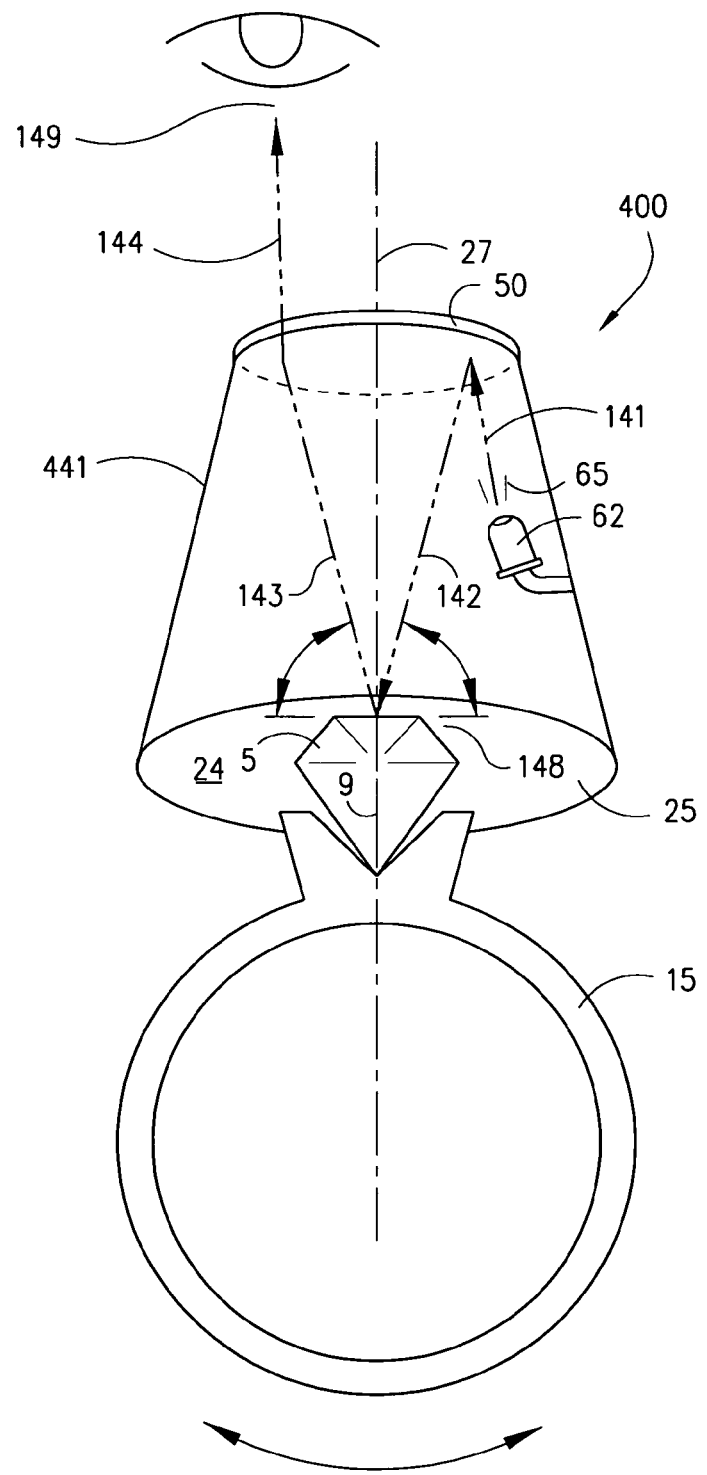
FIG. 10 is a perspective view of a fourth embodiment of the engraved gemstone viewer having a conical housing and a single lens, and with a diamond ring held inside the viewer and hand focused to obtain the mirrored image of the light beam showing the identification number as dark characters given the absence of light.
Figure 11:
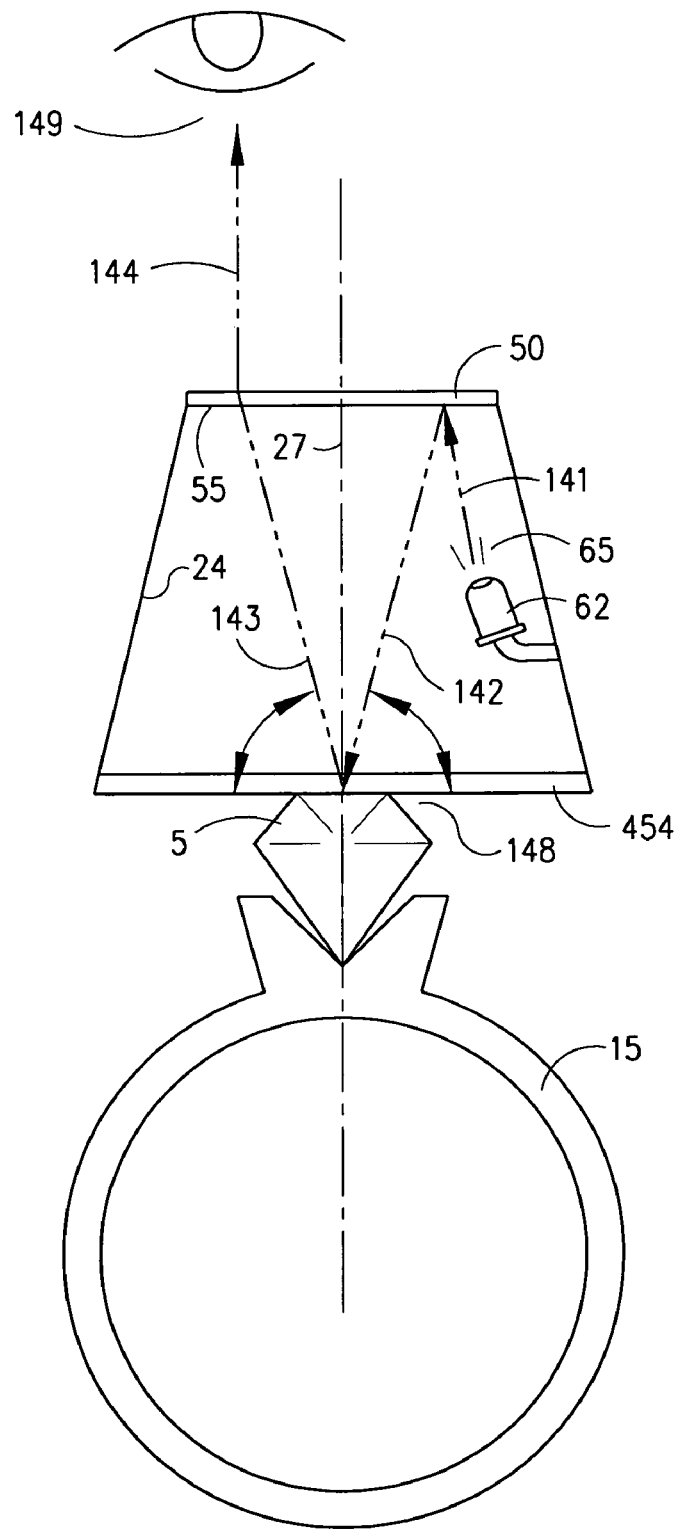
FIG. 11 is a side plan view of a modified version of the fourth embodiment showing the conical housing with a piece of glass at its lower end, and the table of the diamond being pressed against the glass to aid in focusing the viewer to obtain the mirrored image of the table and identification number.

A hand held embodiment of the engraved gemstone viewer 400 is shown in FIGS. 10 and 11. The viewer 400 has conical shell construction that incorporates a conical shell 441 with two ends. The conical shell 441 forms the internal compartment 25 of the viewer 400. The light source 460 is secured to the inside surface of the shell 441. The light source 60 is somewhat similar to that of viewer 20, and includes a conical circuit board shaped to be flushly fixed to the inside surface of the shell 441, holds a battery and is connected to a manual push button switch. A lens 50 is secured to the upper end of the conical shell 441. The lens 50 is of the same general type as in the globe shaped viewer 20, and includes the refection enhancing coating 55. The inside of the viewer 200 includes the light absorbing coating 24. The gemstone 5 or jewelry piece 15 is received into the interior compartment 25 formed by the conical shell 41.

A modified embodiment of container 400 is shown in FIG. 11. This version of the viewer 400 includes a glass plate 454 secured to the end of the conical shell 441 opposite the lens 50. The gemstone 5 is received by viewer 400 by placing its table 6 against the outside surface of the glass plate 454. In both versions, the viewer 400 works better when the center 9 of the gemstone 5 is located slightly off center from the central axis 27 toward the light 62. This offset directs the image 150 through the center of the lens 50. The internal light source 60 is preferably conventional unidirectional LED light 62 of the type in the globe viewer 20. The light source 60 can be several LED lights evenly spaced around the inside of the conical shell 441. The light 62 is aimed in a manner similar to the globe viewer 20. The light paths 141-144 to generate the spectrally reflected image 150 of the light source 60 revealing the inscription 10 on the table 6 of the gemstone 5 is generally the same as above. The gemstone 5 is moved by hand to help bring the table 6 of the gemstone 5 to the focal location 148, and the image 150 and the inscription 10 or identification number 11 into focus.

While the invention has been described with reference to several embodiments, it will be understood by those skilled in the art that various changes may be made and equivalents may be substituted without departing from the broader aspects of the invention.

We claim:

1. An engraved gemstone viewer for viewing a gemstone with a flat, smooth surface, to visibly reveal an inscription, such as an identification number, engraved or etched into the otherwise flat, smooth surface, the inscription being of such a small size as to be invisible to a naked eye, said engraved gemstone viewer comprising:

an opaque container having an outer shell, a viewing portal, an inside surface and an internal compartment, said inside surface being coated with a light absorbing material, and said container being adapted to substantially prevent ambient outside light from striking the flat, smooth surface of the gemstone when the gemstone is cooperatively received by said container;

a magnifying lens having a focal point, said magnifying lens being oriented over said viewing portal to allow viewing of the flat, smooth surface of the gemstone when the gemstone is cooperatively received by said container;

a light source emitting a light directed to travel through said internal compartment of said container along an incident path toward the flat, smooth surface of the gemstone, said light specularly reflecting off the flat, smooth surface to produce specularly reflected light, said incident path and the flat, smooth surface of the gemstone being positioned and oriented to direct said specularly reflected light to travel along a specularly reflected path through said magnifying lens and to a focal point, and a portion of said light traveling along said incident path diffusely reflecting off the inscription and travel away from said specularly reflected path; and, wherein said specularly reflected light produces a light image that reveals the inscription as an absence of light in the image, said image and inscription being viewable at said focal point of said magnifying lens.

2. The engraved gemstone viewer of claim 1, and wherein said light source is located inside said compartment of said container, said light being directed to travel along an initial path toward a transparent surface with a reflective coating, said transparent surface and reflective coating being positioned and oriented to reflect said light to travel along said incident path.

3. The engraved gemstone viewer of claim 2, and wherein said outer shell forms said viewing portal, said reflective surface is said magnifying lens, and said magnifying lens is securely and flushly received by said outer shell to fill said viewing portal, and said container is structured to cooperatively receive the gemstone when the gemstone is mounted on a jewelry piece, and wherein the inscription is an identification number.

4. The engraved gemstone viewer of claim 3, and wherein said container has a gemstone portal, and the gemstone is received by said container by inserting the gemstone through said gemstone portal and into said compartment.

5. The engraved gemstone viewer of claim 3, and wherein said opaque container has a gemstone portal covered by a flat glass plate, and wherein the gemstone is cooperatively received by said container by pressing the flat, smooth surface of the gemstone flushly against said flat glass plate.

6. The engraved gemstone viewer of claim 2, and wherein said container includes cooperating first and second portions, said first and second portions being structured to selectively separate to insert and cooperatively receive the gemstone in said compartment, said first and second portions being further structured to selectively join together to substantially surround the gemstone and block ambient outside light from entering said compartment, and said engraved gemstone viewer including a gemstone support mechanism located inside said container, said gemstone support mechanism having a surface adapted to engage and support the gemstone in a fixed position.

7. The engraved gemstone viewer of claim 6, and wherein said first and second container portions are upper and lower portions, and said gemstone support mechanism is a notch formed by said lower portion, said upper portion forms said viewing portal, and said upper portion is rotatable about said lower portion to focus said light image and inscription.

8. The engraved gemstone viewer of claim 7, and wherein said viewing portal receives a microscope device, said microscope device including said magnifying lens and a second spaced apart magnifying lens, said transparent surface being a glass plate located at one end of said microscope device and positioned inside said compartment of said container.

9. The engraved gemstone viewer of claim 6, and wherein said first and second container portions are upper and lower portions, said magnifying lens is securely and flushly received by said upper portion to fill said viewing portal, and said mechanism for supporting the gemstone includes a removable gripping assembly, said gripping assembly having a gripping portion adapted to engage and hold the gemstone.

10. The engraved gemstone viewer of claim 9, and wherein said lower portion includes a focusing assembly adapted to selectively move the gemstone along a linear path toward said magnifying lens to focus said image and inscription.

11. The engraved gemstone viewer of claim 10, and wherein said container has a central axis, and said focusing assembly and gripping assembly are structured to tilt the table of the gemstone out of normal with said central axis.

12. The engraved gemstone viewer of claim 11, and wherein the gemstone is mounted to a jewelry piece, said container is structured and adapted to cooperatively receive the jewelry piece, and said gripping assembly is adapted to grip the jewelry piece.

13. The engraved gemstone viewer of claim 2, and wherein said light produced by said light source is a beam of light.

14. The engraved gemstone viewer of claim 13, and wherein said light source is an LED light and said beam of light is a substantially unidirectional beam of light.

15. The engraved gemstone viewer of claim 11, and wherein the flat, smooth surface is the table of the gemstone, and said unidirectional beam of light has an effective diameter of about 5 to 6 mm when striking the table of the gemstone.

16. The engraved gemstone viewer of claim 15, and wherein said light source includes multiple lights.

17. The engraved gemstone viewer of claim 1, and wherein the gemstone is translucent.

* * * * *